United States Patent [19]

Murphy et al.

[11] 4,046,002
[45] Sept. 6, 1977

[54] METHOD AND APPARATUS FOR DETERMINING ROTOR LIFE EXPENDED

[75] Inventors: Bartholomew D. Murphy, Marblehead, Mass.; David C. Gonyea, Schenectady, N.Y.

[73] Assignee: General Electric Company, Schenectady, N.Y.

[21] Appl. No.: 738,321

[22] Filed: Nov. 2, 1976

[51] Int. Cl.$^2$ .............................................. G01N 3/00
[52] U.S. Cl. ..................................... 73/116; 73/15.4
[58] Field of Search ............... 73/15 R, 15.4, 15.6, 73/91, 116; 60/39.28 T; 235/151.3

[56] References Cited

U.S. PATENT DOCUMENTS

| | | | |
|---|---|---|---|
| 3,250,901 | 5/1966 | Brahm | 73/15.4 X |
| 3,777,555 | 12/1973 | Petrisko et al. | 73/91 |
| 3,832,893 | 9/1974 | Dlugos | 73/116 |
| 3,908,447 | 9/1975 | Salt | 73/91 |
| 3,950,985 | 4/1976 | Buchwald et al. | 73/116 |

*Primary Examiner*—Herbert Goldstein
*Attorney, Agent, or Firm*—James W. Mitchell; John F. Ahern

[57] ABSTRACT

The useful life of a turbomachine part is affected by cyclic stresses which occur in the turbomachine part as a result of heating and cooling the turbomachine part. Each thermal cycle is comprised of a maximum heating stress and a maximum cooling stress which may occur during turbomachine start-up, load changes, shutdowns, or boiler excursions. The maximum heating stress and the maximum cooling stress for each cycle may be combined to define a stress range. The actual stress range for each cycle is compared with a calculated stress range curve for the turbomachine part to determine the amount of life expended during the cycle for the turbomachine part. This value may be expressed as a percent of life expended for the cycle. The life expended for each cycle is accumulated to provide an output indicative of the total percent life expended for the turbomachine part according to its operating history.

16 Claims, 5 Drawing Figures

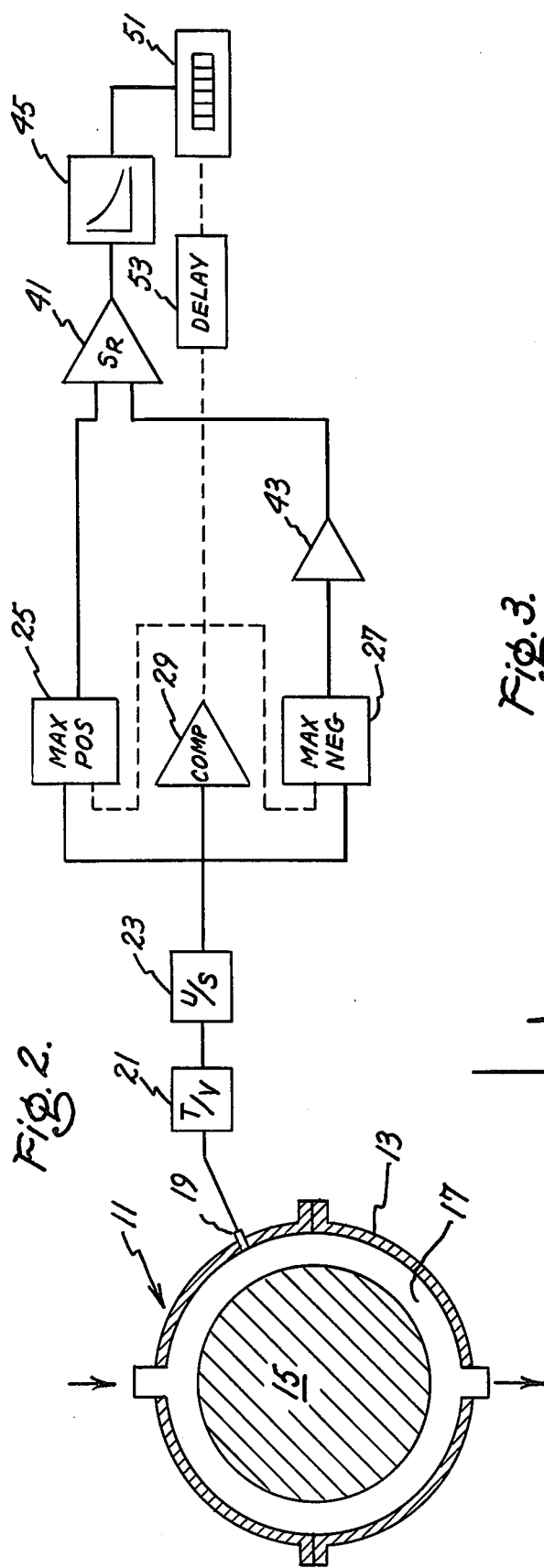

4,046,002

METHOD AND APPARATUS FOR DETERMINING ROTOR LIFE EXPENDED

BACKGROUND OF THE INVENTION

This invention relates, in general, to methods and apparatuses for determining the life expenditure of certain component parts of fluid driven turbomachines; and, in particular, the present invention relates to a method and apparatus for determining the amount of life expended in a turbomachine rotor which is subject to cyclic duty.

The long-term reliability and availability of turbines requires close attention to, and recognition of, the impact of thermal cycles on the "life" of steam turbine components. Excessive thermal transients imposed on turbine rotating and stationary parts during startups, major load changes, and shutdowns can greatly reduce the life of these components. Because the effect of each thermal cycle is usually in itself small, the effects may not be readily apparent to plant operators during the event and may not be recognized and properly considered in making day-to-day operating decisions. However, the long-term cumulative effects of such cycles can result in extended and expensive forced outages requiring major repairs or component replacement.

Prior to this invention, the expenditure of rotor life due to low cycle fatigue caused by thermal stress was regulated by assigning a target for each startup - shutdown cycle. An attempt would be made to control nominal surface stress during the startup, by temperature ramp or computerized stress control, so that the peak stress value would be less than half the allowable stress range for the target life expenditure. This approach erroneously assumes symmetrical startup - shutdown stress cycles and ignores cycles caused by boiler excursions, changes in steam admission modes (full arc to partial arc), or large changes in steady state load. It also requires a level of planning and record keeping which may not be feasible in many plants.

The present invention monitors turbine operating conditions to obtain rotor surface stresses, calculates a stress range for each cycle and outputs the equivalent percent life expended to a non-volatile incremental memory and display. The output information will be valuable in planning plant load distribution and will prove useful in operation by highlighting operating practices or problems which cause large cyclic life expenditures.

U.S. Pat. No. 3,950,985 to Buchwald nd Busse is one example of one prior art practice. In that patent, equivalent hours of operating time for a thermal power plant are determined by actual operating stresses dependent upon operating temperatures. The apparatus of the patented invention sums a calculated stress based on actual turbine temperature with a curve representative of constant service life at that temperature. If the output of the summing junction indicates a higher stress than is permitted under constant service life conditions then an appropriate switching device weights the output of a pulse generator to output an equivalent higher service life used. A digital device counts the equivalent hours of service life expended. While the patented invention is useful in determining component life expenditure due to creep at varying operating temperatures, it fails to recognize low cyclic fatigue duties wherein the resultant stress may be either positive or negative depending on whether the component is a heating or cooling portion of the cycle.

SUMMARY OF THE INVENTION

According to the present invention, the surface stress of a rotor may be determined by knowing the temperature within a turbomachine casing and by knowing the physical properties of the rotor material. An expression for such calculation is given in U.S. Pat. No. 3,446,224 to Zwicky, Jr. As part of the present invention, it has been determined that rotor life is dependent on stress values that are cyclic. By cyclic stress values, it is meant that rotor stresses may be assigned positive or negative values according to whether the stresses are caused by heating or cooling. This, in turn, is determined around a preselected dead band stress in the range of 10 KSI. In a cycle, there will be a maximum positive stress and a maximum negative stress and these two values are used to determine a stress range for a cycle. The stress range for each cycle is then correlated to a graph of stress range versus percent life expended in order to determine the percent of life expended which is then stored into a non-volatile counter which accumulates the life expenditure of the rotor.

OBJECTS OF THE INVENTION

It is one object of the present invention to provide a method and apparatus for determining the cumulative effects of cyclic stresses on the life of a turbomachine rotor.

It is another object of the present invention to provide a method and apparatus for determining the occurrence of a rotor stress cycle.

It is another object of the present invention to provide a method and apparatus for obtaining maximum heating and cooling stress values occurring during each cycle of turbine operation.

It is a further object of the present invention to provide a method and apparatus for determining a stress range for each cycle of turbine operation.

The novel features believed characteristic of the present invention are set forth in the appended claims. The invention itself, however, together with further objects and advantages thereof, may best be understood with reference to the following description taken in connection with the appended drawings.

BRIEF DESCRIPTION OF THE DRAWING

FIG. 2 is a schematic drawing of an apparatus which may be used in carrying out the method of the present invention.

FIG. 3 is a graph indicating the relationship of stress range versus rotor cyclic life expended.

DETAILED DESCRIPTION OF THE INVENTION

In carrying out the method of the present invention it is necessary to monitor an operating condition of the apparatus for which it is desired to determine the amount of life expended. For example, in monitoring the expended life of a turbomachine rotor, the first step in the method is sensing the temperature of the fluid or gas surrounding the rotor which may be carried out by sensing the temperature at the inner wall of the turbomachine casing. After sensing the temperature within the turbomachine casing, it then becomes possible, knowing the material properties of the rotor, to calculate a surface stress for the rotor at the particular temperature or to establish a surface stress profile for the rotor over a period of time as is shown, for example, in FIG. 1. Surface stress calculations may be made in accordance with any known methods and apparatus as, for example, by the method and apparatus shown in U.S. Pat. No. 3,446,224 to Zwicky particularly FIGS. 1 and 4; and, with reference to Column 4, lines 43 to 75.

Figure 1:
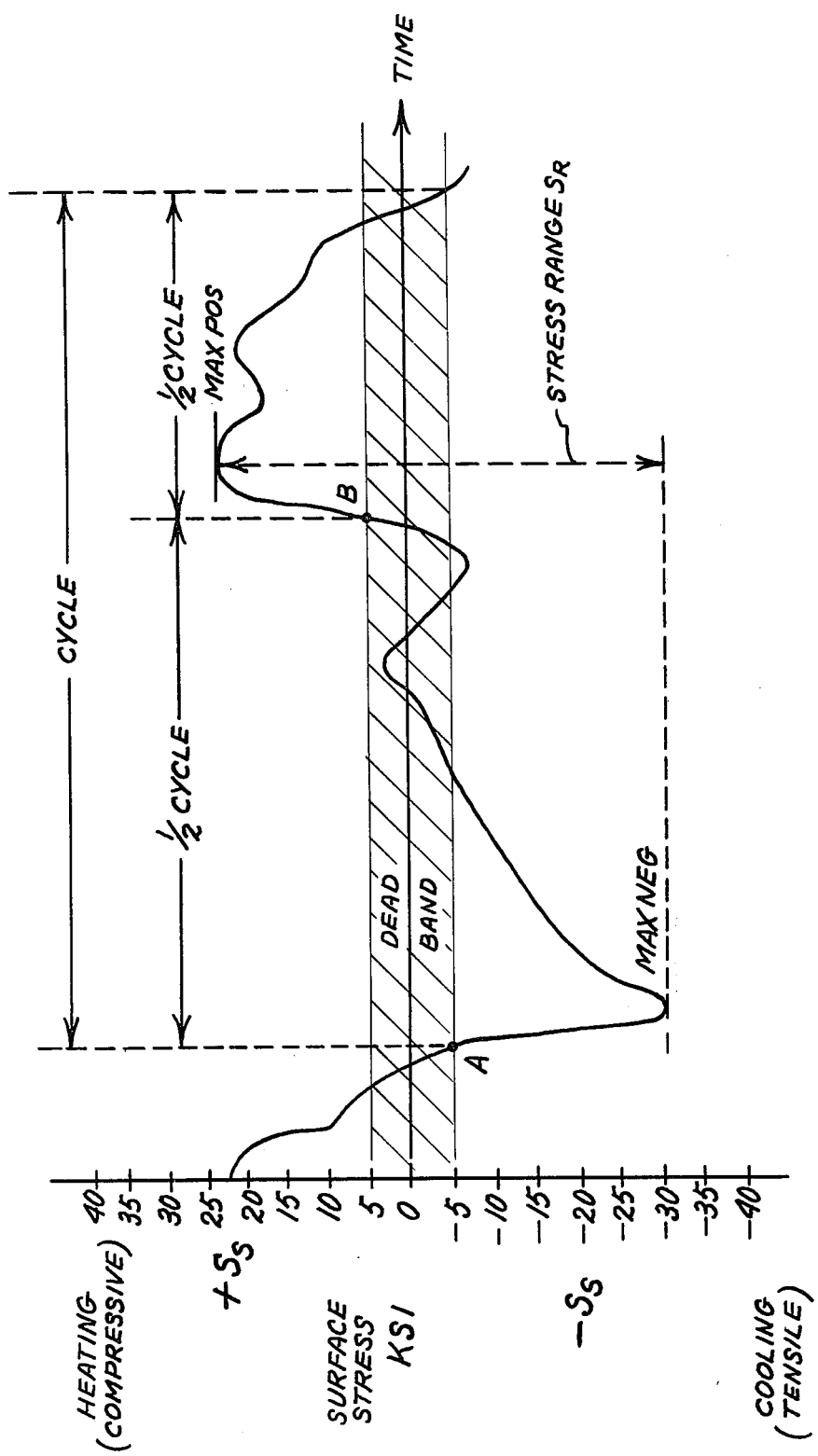
FIG. 1 is a graph indicating a plot stress versus time and showing the occurrence of a single stress cycle of turbomachine operation.

In FIG. 1, of the present invention, surface stress is plotted along a time line to show a cycle of the type which may occur during the operation. Such a cycle includes a cooling half-cycle and a heating half-cycle. For example, at some point during the turbine operation a load change or a boiler excursion may cause the stress occurrence within a turbomachine rotor to go from a positive heating stress to a negative cooling stress or vice-versa. A deadband zone is established around the zero stress line so that relatively small changes in stress direction are not entered into the cyclic count. As the surface stress goes negative below the deadband (point A), the negative stress values are computed to establish a maximum negative stress peak (MAX-NEG) for the half-cycle. The negative half-cycle is completed after the stress curve goes through the deadband zone and enters the positive stress half-cycle (point B). As the surface stress goes positive above the deadband, the positive stress values are computed to establish a maximum positive stress peak (MAX-POS) for the half-cycle. The positive half-cycle is completed after the stress curve goes negative beyond the deadband. Upon completing a full cycle, the maximum positive stress and the maximum negative stress in absolute terms are added together to determine the stress range $S_R$ for the full cycle.

The stress range $S_R$ determines the amount of cyclic life expended for the cycle in which it occurs. Referring briefly to FIG. 3 wherein stress range $S_R$ is plotted against the percent of cyclic life expended, the curve shown represents the theoretical life expenditure for a particular rotor. As will be described in further detail, the stress range determined from FIG. 1 is found on FIG. 3 in order to determine the percent cyclic expended for the particular cycle. The percent life expended for each cycle is then accumulated in a nonvolatile counter to indicate the total life expended for a particular rotor.

FIG. 2 indicates one apparatus for carrying out the present invention. A turbomachine 11 includes a turbomachine casing 13 which surrounds a turbine rotor 15. The annular area 17 between the turbine shell and the rotor is filled with a motive fluid. The motive fluid may be gas from a combustion chamber or steam. The temperature at the inner wall of the turbine shell is measured by a temperature sensor 19 which provides a temperature signal to a temperature to voltage converter (T/V) 21. The temperature to voltage converter is an electronic transducer providing an output voltage proportional to the temperature sensed by the temperature sensor 19. The voltage output from converter 21 is input into a stress calculator 23 which provides an output voltage proportional to rotor surface stress based on the voltage input representative of actual temperature. Such a device is shown in U.S. Pat. No. 3,561,216 to Moore (elements 22 and 23) or in U.S. Pat. No. 3,832,893 to Dlugos et al (element 7). The stress signal output may either be positive or negative as described in conjunction with FIG. 1 of the present invention. The output from the stress calculator 23 is input into storage circuit 25 which stores the maximum positive value, and storage circuit 27 which stores the maximum negative value and voltage comparator 29.

Each storage circuit may comprise an input register which will store the maximum value of the respective positive or negative input signal for the respective positive or negative storage circuit. Each storage circuit may also include an output register which will provide the stored data for transfer to the cyclic counter circuitry to be described. The storage circuit may also include suitable analog to digital converters and digital to analog converters to enable the storage circuit to function in the manner described and all of which is well known to persons skilled in the art. On the other hand, elements 25 and 27 may be tracking amplifiers which will store maximum stress values in either the positive or negative directions respectively.

Voltage comprator 29 is electronically preset to provide an output voltage whenever the negative half-cycle of the stress range is initiated, i.e., voltage comparator will set to an on signal whenever the negative deadband limit (for example 5000 psi) is followed by a more negative input. It should be realized that although one embodiment of the present invention is being described in terms of the comparator output occurring during the initiation of a negative half-cycle, it is also possible to reverse the system logic so that the comparator will output a signal upon the initiation of the positive half-cycle and that such a modification would be obvious to one having skill in the art. Voltage comparator 29 functions to reset storage circuits 25 and 27 by either moving data from an input register to an output register in a digital storage circuit or by resetting tracking amplifiers to zero in an analog storage circuit. Voltage comparator 29 is also used to enable a counter 51 for the purpose of receiving stored information as will be explained. Voltage comparator 29 will reset to the off state whenever the positive deadband is exceeded.

The respective outputs from the maximum positive storage circuit and the maximum negative storage circuit are input into a summing amplifier 41. The output from the maximum negative storage circuit 27 is changed from negative to positive in inverter amplifier 43. The two inputs to summing amplifier 41 will produce an output signal proportional to the stress range $S_R$ for the cycle. It is the stress range for each cycle which is determinative of the cyclic life expended during each cycle.

Referring to FIG. 3, a graph is plotted showing stress range versus percent cyclic life expended. The curve represents a theoretical calculation for a particular rotor which relates stress range to the percent life expended for each cycle. The curve is based on rotor geometry and material and may be approximated by the following expression:

Percent Life Expended = $C_0 + C_1(S_R) + C_2(S_R)^2 + C_3(S_R)^3$ whenever $S_R$ is greater than the threshold value.

Below the threshold value there is no count output. Hence, the stress range $(S_R)$ obtained as previously described is compared with the theoretical curve shown in FIG. 3 to obtain the percent of cyclic life expended. The threshold value is established on the basis of a calculated allowable stress range for a particular rotor and if the actual stress range is less than the threshold stress range then no count will be taken.

The curve shown in FIG. 3, may be input into a cyclic life expended calculator 45. The calculator 45 electronically simulates the graph shown in FIG. 3 and compares the input of the actual stress range with the simulated curve to output a percent value for life expended.

The output from the cyclic life expended calculator is input into a non-volatile counter 51 which accumulates the counts of cyclic life expended. A non-volatile counter is a counter which will always hold the count input even under conditions of power failure. The counter is tied to the voltage comparator 29 through a delay circuit 53 so that sufficient time is allowed for clearing data through the storage circuit so that the output data is available when counter 51 is enabled.

The aforesaid circuit may be further described as follows: means for measuring the temperature adjacent the rotor surface (temperature sensor 19 and temperature to voltage converter 21); means for calculating rotor stress (voltage to stress converter 23); means for storing a maximum positive and a maximum negative stress for each cycle (storage circuits 25 and 27); means for determining the occurrence of a cycle (comparator 29); means for determining a stress range for each cycle (summing amplifier 41); means for determining the life expended for each cycle (life expended calculator 45) and means for accumulating the total life expended for the rotor (counter 51). While the foregoing invention has been described for determining rotor life expenditure, it is obvious that the same may be done for other turbine parts including rotor buckets and shells.

Figure 4:
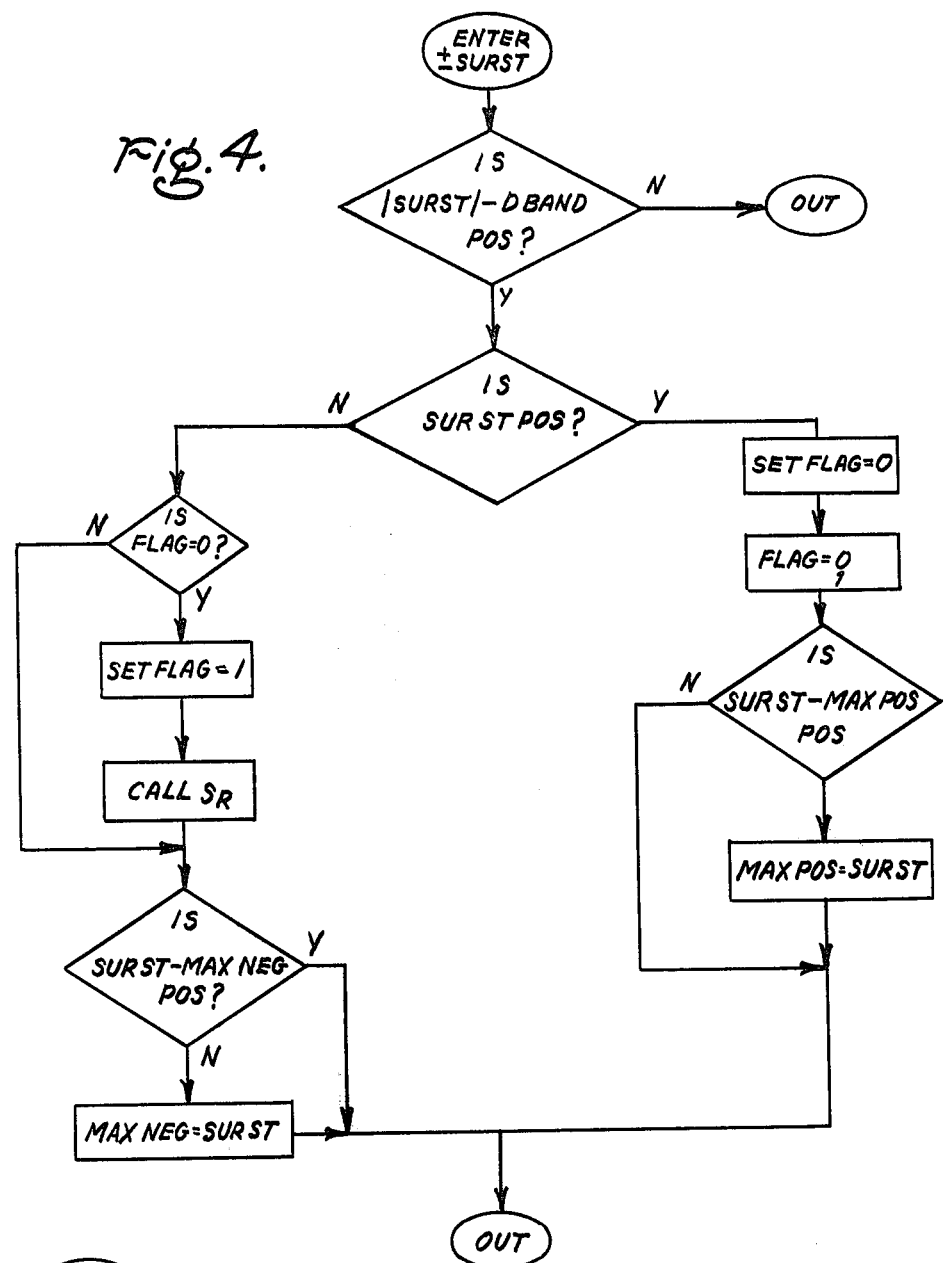
FIG. 4 and 4A are flow charts which show the method of calculating the accumulated life expenditure for input stress values.
Figure 4A:
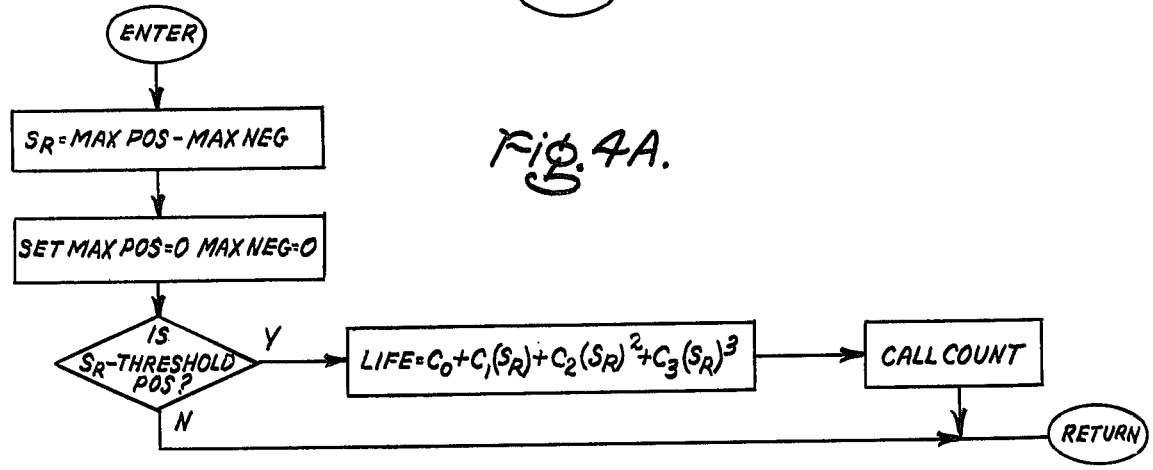

Referring to FIGS. 4 and 4A, a flow chart is shown illustrative of the method of the present invention and also illustrative of a program which may be combined with computer technology known to those having ordinary skill in the art. Preliminary to entering the flow chart of FIG. 4 are the steps of measuring the temperature of a turbomachine and calculating therefrom a positive or negative surface stress (± Sur ST). Without belaboring that which is obvious from the flow diagram, the entered surface stress (± Sur ST) is checked to ascertain whether or not it is out of the deadband. Thereafter, the surface stress is input either into a first channel to store a maximum negative surface stress or into a second channel to store a maximum positive surface stress. The stored values are retained until a new negative half-cycle is begun whereupon a stress range $S_R$ calculation is called as shown in FIGS. 4 and 4A. In FIG. 4A it is noted that when the stress range calculation begins MAX-POS and MAX-NEG are reset to zero. In the stress range calculation, the question is asked as to whether the stress range minus the threshold from FIG. 3 is positive. If the answer is yes, a count of life expended is computed. If the answer is no, there is no count output. While the present example assumes that a stress cycle begins on the negative half-cycle, it is clear that it would be obvious to one of ordinary skill in the art to begin the stress cycle on the positive half-cycle. The flag box and its associated flag signals comprise logic means to insure that a cycle has taken place prior to a report to stress range calculation.

In practicing the present invention, the following method steps are used:

1. Sensing the temperature in a turbomachine casing adjacent the rotor surface;

2. Determining a rotor stress from the temperature;

3. Determining whether the rotor stress is inside or outside the deadband zone;

4. Storing a maximum negative stress and a maximum positive stress for each thermal cycle;

5. Combining the absolute values of the maximum negative stress and the maximum positive stress to determine a stress range for each cycle;

6. Comparing the stress range with a threshold stress range;

7. Determining the cyclic life expended for each cycle;

8. Accumulating the cyclic life expended history of the rotor.

While there has been shown what are considered to be the preferred embodiments of the invention, it is recognized that other modifications may be made therein, and it is intended to cover in the appended claims all such modifications as fall within the true spirit and scope of the invention. For example such modifications may include logic modifications whereby a stress cycle is counted during the initiation of the heating (positive) half-cycle rather than during the initiation of cooling (negative) half-cycle as shown. Further, the invention has been illustrated as a method of determining rotor life expended whereas the invention is not limited to rotors and may be used to determine the life expended of other turbomachine parts such as shells, casings, buckets and bucket wheels. While the resultant output of the counter indicates percent of life expended it may be used to indicate percent of life remaining or any other indication of the amount of component life which has been used or remains useful. Finally, it is recognized that stress may be easily related to strain by a material constant and that it is not absolutely necessary to utilize temperature to measure cyclic duties.

What is claimed is:

1. A method for determining the life expended for a turbomachine part based upon cyclic duties imposed on the turbomachine part comprising the steps of:

determining a stress versus time curve for the turbomachine operation;

identifying a stress cycle including a maximum heating stress and a maximum cooling stress;

combining the maximum heating stress and the maximum cooling stress for each cycle to determine a stress range for the cycle;

comparing the stress range for each cycle with a calculated curve representing stress range versus life expended to determine the life expended for each cycle; and, accumulating the cyclic life expended for each cycle to determine the total life expended for the turbomachine part.

2. The method recited in claim 1 wherein determining a stress versus time curve for turbomachine operation comprises the steps of:

measuring, at least, the approximate temperature of the turbomachine part over a period of time; and, calculating stress from the measured temperature during the time period.

3. The method recited in claim 1 further comprising the steps of:

measuring, at least, the approximate temperature of the turbomachine part;

calculating a positive or negative stress half-cycle depending on whether the turbomachine part is heating or cooling;

determining a maximum positive stress and a maximum negative stress for the heating and cooling half-cycle respectively; and, storing the maximum negative stress and the maximum positive stress for each cycle.

4. The method recited in claim 1 wherein the identifying step further comprises:

measuring the stress values against a preselected deadband to determine whether or not the stress value will be reported.

5. The method recited in claim 1 wherein the comparing step further comprises:

measuring the stress range values against a preselected threshold stress range to determine whether or not the stress range will be reported.

6. The method recited in claim 1 further comprising the steps of:

comparing the stress range for each cycle with a calculated stress range versus percent life expended to determine a percent life expended for each cycle; and, accumulating the percent life expended for each cycle to determine the total percent life expended for the turbomachine part.

7. A method for determining the life expended for a turbomachine rotor based upon cyclic heating and cooling of the rotor comprising the steps of:

measuring the temperature adjacent the rotor surface;

calculating a positive stress half-cycle and a negative stress half-cycle depending upon whether the rotor is heating or cooling;

storing a maximum positive stress and a maximum negative stress to determine the occurrence of a cycle;

combining the maximum positive stress and the maximum negative stress for each cycle to determine a stress range for the cycle;

comparing the stress range for each cycle with a calculated curve representing stress range versus life expended to determine the rotor life expended for each cycle; and, accumulating the cyclic life expended for each cycle to determine the total life expended for the rotor.

8. The method recited in claim 7 further comprising the step of:

determining whether a negative or positive stress has exceeded a deadband value to determine whether the stress will be reported for storage.

9. The method recited in claim 7 further comprising the step of:

determining whether the stress range for the cycle exceeds a threshold stress range to determine whether the stress range will be reported for accumulation.

10. An apparatus for determining the expended life of a turbomchine part comprising:

means for measuring at least the approximate temperature of the turbomachine part;

means for calculating stress in the turbomachine part from the measured temperature, said calculated stress being positive or negative depending upon whether a heating half-cycle or a cooling half-cycle is taking place;

means for determining the occurrence of a cycle;

means for storing a maximum negative stress and a maximum positive stress for each cycle;

means for calculating a stress range for each cycle by summing the maximum positive stress and the maximum negative stress absolute;

means for comparing the stress range for each cycle with a curve representing a calculated stress range versus life expended to determine the life expended for each cycle; and, means for accumulating the life expended for each cycle to determine a total life expended for the turbomachine part.

11. The apparatus recited in claim 10 wherein the means for determining the occurrence of each cycle comprises a voltage comparator having an output signal whenever maximum positive and negative stresses are stored and a deadband is crossed.

12. The apparatus recited in claim 10 wherein the means for determining the occurrence of each cycle comprises a logic circuit having an output signal whenever maximum positive and negative stresses are stored and a deadband is crossed.

13. The apparatus recited in claim 10 further comprising means for measuring an input stress against a deadband to determine whether the input stress should be reported for storage.

14. The apparatus recited in claim 10 further comprising means for measuring the stress range against a threshold stress range to determine whether the stress range should be reported to count.

15. The apparatus recited in claim 10 wherein the accumulating means is a counter with a non-volatile memory.

16. The apparatus recited in claim 10 wherein the output of the accumulating means is the percent life expended of the turbomachine part.

* * * * *